(12) United States Patent
Helmlinger (10) Patent No.: US 6,772,915 B2
(45) Date of Patent: Aug. 10, 2004

(54) DISPENSER FOR MEDIA

(75) Inventor: Michael Helmlinger, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 82 days.

(21) Appl. No.: 10/072,142

(22) Filed: Feb. 7, 2002

(65) Prior Publication Data

US 2002/0117513 A1 Aug. 29, 2002

(30) Foreign Application Priority Data

Feb. 28, 2001 (DE) .......................................... 101 10 742

(51) Int. Cl.$^7$ ................................................. B67D 5/33
(52) U.S. Cl. ..................... 222/153.13; 222/82; 222/326
(58) Field of Search .................... 222/82, 83.5, 153.13, 222/160, 162, 326

(56) References Cited

U.S. PATENT DOCUMENTS

| | | | | |
|---|---|---|---|---|
| 2,771,879 A | * | 11/1956 | Salisbury | 604/214 |
| 3,512,524 A | * | 5/1970 | Drewe | 604/192 |
| 3,938,514 A | * | 2/1976 | Boucher | 604/28 |
| 4,077,548 A | | 3/1978 | Beard | |
| 4,131,217 A | * | 12/1978 | Sandegren | 222/82 |
| 4,349,129 A | * | 9/1982 | Amneus | 222/41 |
| 5,836,922 A | * | 11/1998 | Hansen et al. | 604/214 |
| 6,315,761 B1 | * | 11/2001 | Shcherbina et al. | 604/216 |
| 6,446,839 B1 | * | 9/2002 | Ritsche | 222/82 |

FOREIGN PATENT DOCUMENTS

| | | |
|---|---|---|
| DE | 39 09 820 A1 | 9/1990 |
| DE | 197 00 437 A1 | 7/1997 |
| DE | 199 05 993 A1 | 8/2000 |

* cited by examiner

*Primary Examiner*—Gregory L. Huson
*Assistant Examiner*—M A Cartagena
(74) *Attorney, Agent, or Firm*—Quarles & Brady LLP (57) ABSTRACT

Such dispensers must be easy to grasp or operate by a user, e.g. a user suffering from rheumatoid arthritis and whose capacity to manipulate objects is under certain circumstances limited. In addition, the dispenser must have a simple, inexpensive construction from a minimum number of components.

The dispenser is used for the discharge of media, particularly fluids, e.g. a liquid, which preferably contain a pharmaceutical substance, as described in exemplified manner hereinbefore. In the case of the dispenser, the medium is discharged in at least two proportioned partial charges by actuating an actuating means. As a result of the actuation of the actuating means, a relative movement is produced between the actuating means and a housing having a dispenser discharge opening. According to the invention an elastically deformable material bridge is provided. The actuating means is held on the housing by means of the elastically deformable material bridge.

20 Claims, 9 Drawing Sheets

2. Hub

DISPENSER FOR MEDIA

FIELD OF THE INVENTION

The present invention relates to a dispenser for media, particularly for fluids and preferably liquids containing at least one pharmaceutical substance.

Such dispensers for media, in which there is usually an atomized discharge of the medium, e.g. in dosed (portioned) form, are known for the application or administration of the most varied media to the most varied locations. It is in particular known to carry out an atomized discharge of the medium in the area of the nose, in order to apply medicaments to the nasal mucosa. All types of medicaments can be involved, whose pharmaceutical substances are absorbed by the body via the nasal mucosa or respiratory tracts. Over and beyond the possibility of precisely dosing the medicaments, it is also possible using such dispensers to apply medicaments, whose active substance dosage can be critical, such as e.g. opiates. Such dispensers can also be used for the administration in precisely dosed form of anti-migraine agents and similar active substance groups. However, such dispensers are also suitable for the discharge of media with active substances used in the treatment of rheumatoid arthritis. Such dispensers must be easy to grasp and operate by a user, e.g. a user suffering from rheumatoid arthritis and whose capacity to manipulate articles may in certain circumstances be limited. The dispensers must also have a simple and inexpensive construction from a minimum number of parts.

The dispenser is suitable for the discharge of media, particularly fluids, e.g. a liquid, which preferably contain a pharmaceutical active substance or agent, such as has been specified in exemplified form hereinbefore. With the dispenser the medium is discharged in at least two proportioned partial charges through the actuation of an actuating means. The actuation of the actuating means produces a relative movement between the actuating means and a housing having a dispenser discharge opening. According to the invention an elastically deformable material bridge is provided by means of which the actuating means is held on the housing. On actuating the actuating means for producing a medium discharge, the material bridge is pretensioned by deformation.

According to a further development of the invention, the relaxing of the material bridge at the end of the actuation of an actuation-opposed return stroke is produced automatically.

It is advantageous for the material bridge to be formed from at least one web which, in the relaxed state, has a curved configuration. If e.g. the web is made from a plastics material, this can be produced by a corresponding shaping during manufacture. Precurving is a simple way of producing an elastically deformable element. Particular advantage is obtained by constructions in which the at least one web is approximately arcuate in the relaxed state. It is also possible to use ellipsoidal shapes or the like. However, the virtually arcuate shape has the advantage that the deforming forces to be absorbed are uniformly distributed in the web and consequently different loads do not have to be absorbed in different areas of the web.

According to a preferred development of the invention, there are at least two webs, which are then uniformly distributed in rotationally symmetrical manner around the central axis.

At least on the end facing the housing, the webs can meet in an annular section, which is referred to as a ring section.

The webs in particular project in ray-like manner from the ring section, it is advantageous for the curvature of the webs to be chosen in such a way that the webs are oriented radially in the plane of the ring. According to an advantageous development of the invention, the ring section is supported on the dispenser housing. It can in particular be undetachably connected to the housing. The undetachable connection of the ring section to the housing can e.g. be brought about by welding, bonding or some other type of fixing or also by a one-piece construction of the ring section, housing and webs. According to alternative developments it is possible for the ring section facing the housing to be detachably fixed to the housing.

It is possible to provide on the ring section a guide sleeve, which is constructed coaxially to the central axis and projects into the interior of the housing. This sleeve can on the one hand be used for fixing the ring section to the housing and on the other also to form a guide for discharge device elements which can be placed within the housing. It is in particular possible for it to influence and/or guide the path of an actuating movement of the actuating means during a discharge stroke (actuating stroke). It can in particular hold link paths, guide links and locking means or means limiting the travel of the actuating stroke.

According to a further development of the invention, the material bridge is constructed as a bellows. The bellows preferably has a coiled folding edge configuration, which leads to a spiral spring contour-like configuration of the folding edge.

According to preferred developments of the invention, the material bridge is made from a plastics material, particularly a breaking-resistant, preferably elastically deformable plastic. It is particularly advantageous for the material bridge to be made from the same material as the dispenser housing or from at least one material, which is processable with the housing material in a multicomponent injection moulding process. In the design of the material webs it must be ensured that the actuating force on producing the dispenser discharge stroke is not immoderately increased by the material bridges.

It must simultaneously be possible to produce an adequate number of load applications in the dispenser, without there being a change to the behaviour of the material webs impairing operation. In particular, the material webs must be elastically deformable to the extent required for producing a discharge stroke. Simultaneously the forces built up through the bracing action (deformation of the material webs) must be sufficiently high to ensure that a return stroke of the actuating element takes place automatically and optionally also during the return stroke locking means must be released, pressed over or travelled over.

According to a development of the invention, the storage chamber of the container used for storing the medium is constructed as a pump chamber of a thrust piston pump. The thrust piston is preferably constructed as a plug sealing the pump chamber and in the housing there is a discharge channel leading to the discharge opening serving as a piston rod. During the first actuation, the plug is perforated by the correspondingly constructed discharge channel (needle point) and in this way the connection is formed between the pump chamber and the discharge opening. Then, during the further actuation of the dispenser, action occurs on the piston in such a way that it is moved in the sense of reducing the pump chamber volume and as a result medium is discharged through the dispenser discharge opening.

According to a preferred development of the invention, the storage container is held in a sleeve, the latter being displaceably guided with respect to the control device.

It is advantageous for the dispenser to be constructed in such a way that the container with the storage chamber can be introduced through an opening into the dispenser, the opening being in particular a ring section, which is constructed on the actuating means side and whose central axis is preferably coaxial to the central axis of an external ring section. Through such an opening, which can also be coverable, it is possible to initially almost completely produce the dispenser, assemble the same and then introduce the container with the stored medium into the assembled dispenser. This is on the one hand advantageous, because then in the pharmaceutical filling company there is no need to carry out any further assembly or fitting of the dispenser and instead the filled storage containers merely have to be inserted into the dispensers. On the other hand it is possible to provide the dispenser just prior to use with a storage container with the medium to be discharged. This can e.g. be advantageous if the active substance to be discharged must be stored in cooled or refrigerated form. In this case the volume of the parts to be cooled is reduced to the container volume, because the dispenser can be separately stored. Constructions are also conceivable where the storage container can be removed again from the dispenser and using the same dispenser and new, filled containers further, clearly defined partial medium charges can be discharged. This provides a reusability of the dispenser. The latter is particularly advantageous if the stored medium does not have a long term storage stability and it is consequently desirable to discharge the medium, e.g. in two partial charges, where a new medium container is then used for the next two partial charges.

In the case of a dispenser according to the invention, it is advantageous to construct locking and/or stop means acting at least indirectly between the actuating means and the housing and which at least serve to limit an actuating stroke. For the discharge of clearly defined partial charges, it is necessary to precisely define the actuating path of an actuating stroke. This can be advantageously achieved with the corresponding locking and/or stop means, which do not necessarily act directly between the actuating means and the housing. Instead this action can also be indirectly produced, e.g. in that the storage container is held in a sleeve, the actuating means acts on the storage container or the sleeve and the locking and/or stop means are constructed to act between the housing and the sleeve. By means of locking and/or stop means at least indirectly acting between the actuating means and the housing, it is possible to oppose a return stroke of the pump chamber during the automatic return stroke of the actuating element. This is more particularly necessary if the dispenser in question has a plunger pump, whose pump chamber simultaneously acts as a storage container.

According to developments of the invention, locking means acting at least indirectly between the actuating means and the housing are provided and which must be pressed over for producing an actuating stroke of the actuating element. They can in particular be elements having nominal breaking points and which by the tearing away of the latter release the actuating stroke. This possibility must in particular be provided if it is to be ensured that an actuating force is applied, which is sufficient for completely performing an actuating stroke. The possibility of pressing over the locking means is then selected in such a way that the necessary force is also sufficient to completely pass through an actuating stroke of the actuating element and prior to the end of the actuating stroke the user no longer has time to terminate actuation prior to the complete performance of a discharge stroke.

According to an advantageous development of the invention, the material bridge serves as an actuating means. This has the advantage that only a very small number of components is required for producing the dispenser. It is advantageous if the area of the material bridge engaging on the housing is constructed as a back-stop.

In alternative constructions, it is also possible for the material bridge to be surrounded by an actuating element in the area not covered by the housing. This construction has the advantage that the function of the material bridge cannot be destroyed by external action thereon. A completely closed housing is created, in which the material bridge is enclosed.

In order to apply to the dispenser in simple manner an opposing force counteracting the actuating force and in order to make the dispenser suitable for single-handed operation, it is advantageous to construct a back-stop on the housing.

BRIEF DESCRIPTION OF THE DRAWINGS

These and further features can be gathered from the claims, description and drawings and the individual features, both singly or in the form of subcombinations, can be implemented in an embodiment of the invention and in other fields and represent advantageous, independently protectable constructions for which protection is here claimed. These and further developments of the invention can be gathered from the claims, description and drawings. The invention is also illustrated by the following embodiments and the attached drawings, wherein show:

DETAILED DESCRIPTION OF THE DRAWINGS

Figure 1:
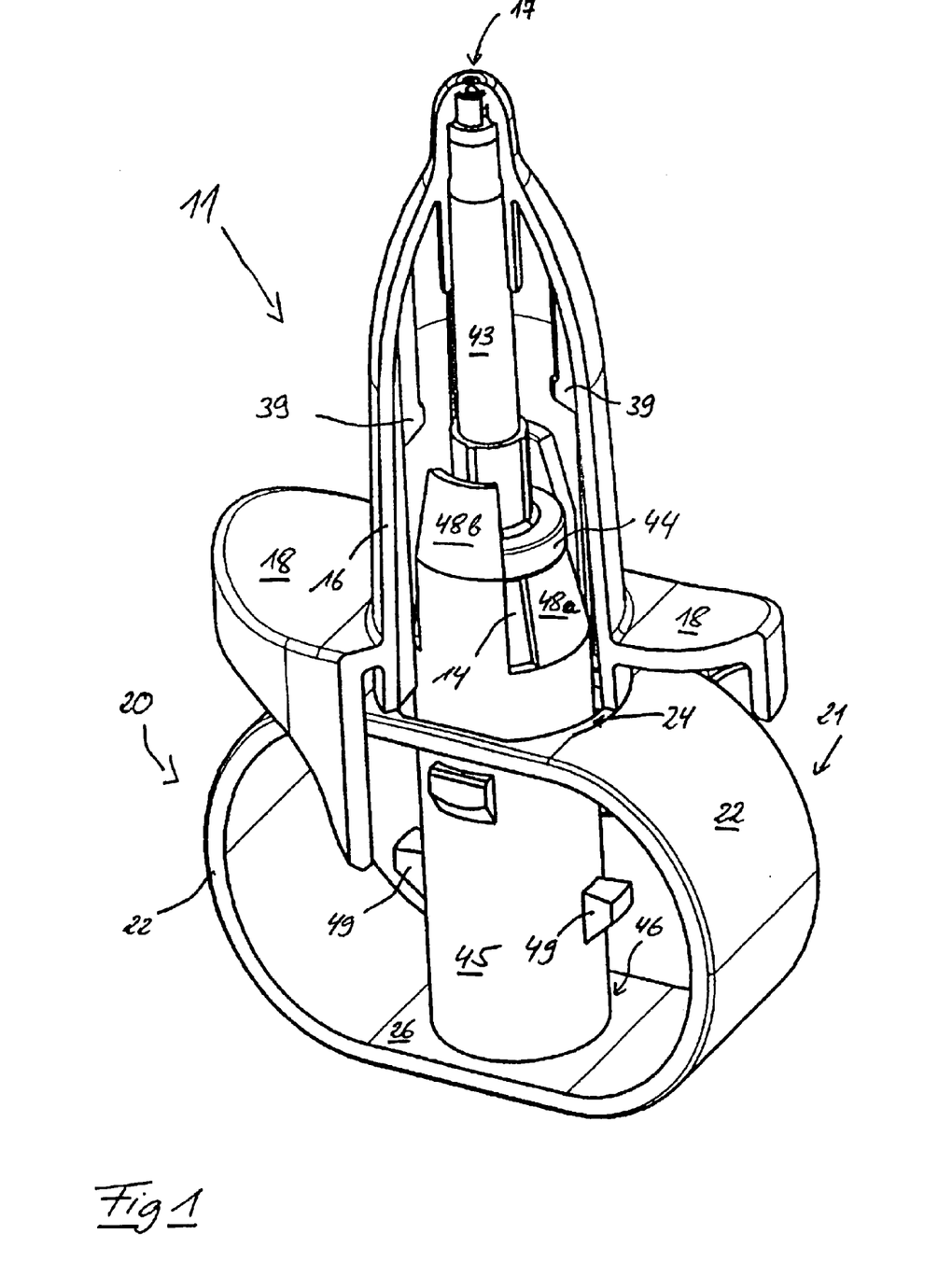
FIG. 1 A first embodiment of a dispenser according to the invention in part sectional form.

FIG. 1 shows in part sectional form a first embodiment of a dispenser 11 according to the invention. The dispenser has a housing 16 on which are constructed in laterally projecting manner the back-stops 18. The discharge opening 17 formed in the casing 16 can be connected to the storage chamber of a container 14 in that the discharge channel constructed in the piston rod 43, which is fixed on the housing side, perforates with a tip or point a plug retained in the container.

In a ring section 24, the actuating means 20, formed by diametrically facing webs 22, which are semiarcuately curved, is fixed to the housing. The free internal diameter of the ring section 24 is larger by an allowance than the external diameter of a sleeve 45 in which the container 14 is held. The container 14 is held in the sleeve by means of dropped holding webs 48, which face the container and inwardly engage behind the container edge 44. In the sleeve 45 are constructed holding webs 48a, which hold the container 14 in the sleeve 45 prior to a first actuation, whereas the second holding webs 48b hold the container before the second actuation. The dispenser serves to discharge the medium stored in the container 14 in two, more particularly equal, portioned partial charges.

In addition, on the outside of the sleeve are constructed detents 47, which in conjunction with the inner edge of the ring section 24 ensure that an actuation of the dispenser can only take place if the actuating force is so high that there is a pressing over counteracting the locking action of the detents 47 on the inner edge of the ring section 24. On their rear side remote from the ring section in the unactuated rest position, the detents 47 are provided with bevels, so that during the return stroke it is possible to achieve a very low resistance passing through of the ring section 24.

Between the ring section 24 and the base, which also has a ring section, extend the material sections of the actuating means constructed as webs 22. The base 26 is constructed as a flat, narrow area surrounding the ring section 46. The webs 22 are constructed as band-shaped strips and lead from the actuating element-side ring section 46 to the housing-engaging ring section 24. The ring section 24 can be both detachably and undetachably fixed to the housing 16. It is alternatively possible for the ring section 24 to be shaped onto the casing 14 and appropriately connected thereto.

The sleeve 45 is fixed to the actuating means 20 in the vicinity of the base 26 with its internal diameter corresponding to the free diameter of the ring section 46. For actuating the dispenser the operator grasps it in that he initially places fingers on the back-stop 18 constructed on the housing side. The user can then either e.g. place the thumb on the base 26 or also the inside of the hand surface and thereby hold the dispenser 11 in one hand and operate it in that a force is applied between the fingers resting on the back-stops 18 and the parts of the hand acting on the base 26. On actuating the dispenser, firstly the band-shaped webs 22 are deformed and pretensioned in that the radius of curvature is reduced and consequently there is a more pronounced curvature of the webs. During the first actuation of the dispenser, the detents 47 initially engage with the ring section 24. The holding webs 48a engage behind the edge 44 of the container 14, so that the latter is carried along by the sleeve 45 during its further movement. As soon as the actuating force on the actuating means 20 is high enough to press over the holding back action of the detents 47 on the container edge 24, through the actuation the sleeve 45 is moved further in the direction of the discharge opening 17 in the housing 16. With the holding web 48a engaging behind it, the container 14 is simultaneously moved further in the direction of the discharge opening 17. The tubular body constructed as a piston rod 43 and located within the housing is inserted in the interior of the container 14. The needle constructed at its lower end perforates the plug held in and sealing the container 14. During the further movement the piston rod 43, which has in its interior a discharge channel, is further inserted in the container and moves the plug sealably held therein further downwards. The end of the movement takes place when the stops 49 engage with the ring section 24 and consequently prevent a further movement of the sleeve 45 towards the discharge opening 17. During this movement the plug in the housing 14, constructed as a pump chamber, is moved further downwards, so that there is a reduction to the pump chamber volume. The fluid displaced by the volume reduction passes through the discharge channel to the discharge opening 17 and is there e.g. discharged in atomized form. During this movement the material bridge 21, formed from the webs 20 and ring sections 24, 26, is pretensioned by deformation.

As soon as actuation is ended and the actuating force acting on the actuating means 20 declines, there is an automatic return stroke of the sleeve 45 in that the material webs attempt to return to their initial position and the stored deformation energy is thereby reversed. The sleeve slides rearwards with respect to the container 14, because the latter is held in its partial actuation end position by means of the frictional forces acting between the container inner wall and the guide elements of the piston rod 43, as well as by means of the forces acting between the container inner wall and the plug, as well as the discharge channel needle and the plug. The inwardly projecting, front holding webs 48b slide rearwards back over the container edge 44 and engage behind the same for the next actuation. The detents 47 are again moved into a position which, considered in the discharge direction, is behind the ring section 24. The container is now ready for a second discharge of medium, which can in particular an equal medium portion to that during the first discharge can be discharged. The discharge process takes place in the same way as during the first discharge, except that obviously there is no longer any need to perforate the plug, because this has already taken place. The holding webs 48b engage behind and move inwards the container 14 and the container edge 44 arrives in a position in which it forwardly travels over the gripping elements 39. Following the second and final actuation of the dispenser 11, the function of the gripping elements 39 is to hold the container 14 in such a way that it cannot be moved back rearwardly again and thereby give the impression that a further discharge on the part of the dispenser is still possible.

Figure 2:
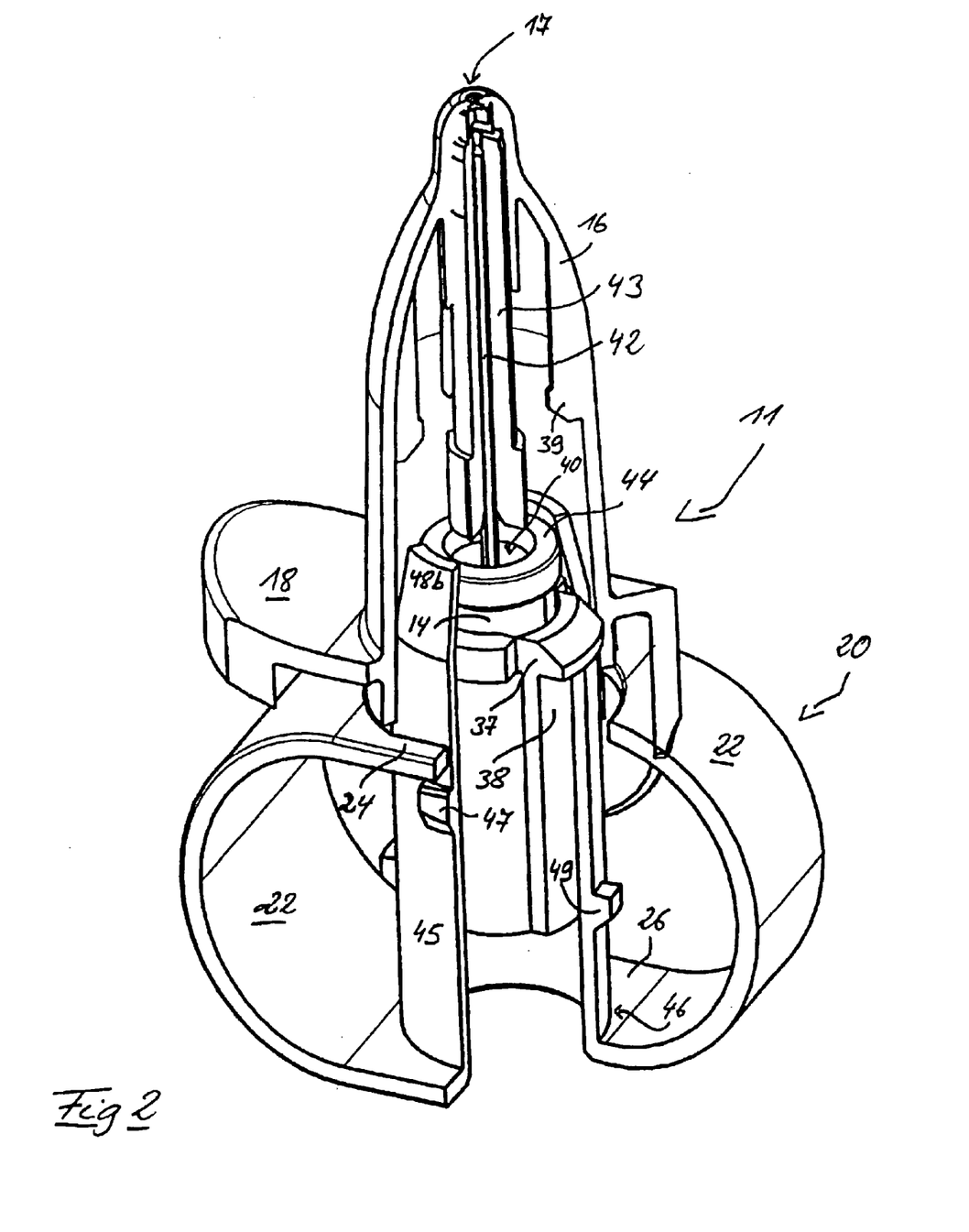
FIG. 2 A part sectional representation of a second embodiment of the invention.

FIG. 2 shows in part sectional representation a second embodiment of a dispenser according to the invention, which essentially corresponds to the first embodiment, so that reference will only be made hereinafter to the features differing compared with the embodiment shown in FIG. 1 and reference is otherwise made to the description concerning FIG. 1. In FIG. 2 the sleeve 45 and piston rod 43 with the discharge channel 42 are shown in part sectional form, in the same way as represented in FIG. 1.

In the embodiment of FIG. 2 the dispenser 11 also has a housing 16, which is provided with a discharge opening 17 to which leads the discharge channel 42, which is constructed within the piston rod 43 of a thrust piston pump. In the interior of the housing there are gripping elements 39, which engage behind the edge 44 of the container 14, after the final, portioned partial discharge has taken place. Here again on the sleeve 45 are constructed stops 49, which serve as a stroke limiting and stop means for the actuating stroke path and which act indirectly between the actuating element, namely the actuating means 20, constructed as webs 22 and the housing. In addition, as locking means are provided the detents 47, which act at least indirectly between the actuating element 20 and the housing 16 and whose action must be overcome in order to produce a dispenser actuating stroke.

Unlike in the embodiment according to FIG. 1, not only is there a sleeve 45 into which can be introduced the storage chamber 15, i.e. the container 14, but between the sleeve 45 and the container 14 is also provided a ring body 38. The ring body 38 serves on the one hand to receive the container 14 and on the other with the inserted container 14 can also be introduced easily into the dispenser 11, which is otherwise preassembled or finished. In order to hold the ring body in the sleeve 45, the latter has locking means 37. The locking means 37 lock with a corresponding recess or with the upper edge of the sleeve 45 and consequently reliably ensure that there is no removal of the container 14, unless it is intentionally or unintentionally removed. This also provides a simple possibility for the fixing of the container.

Figure 3A:
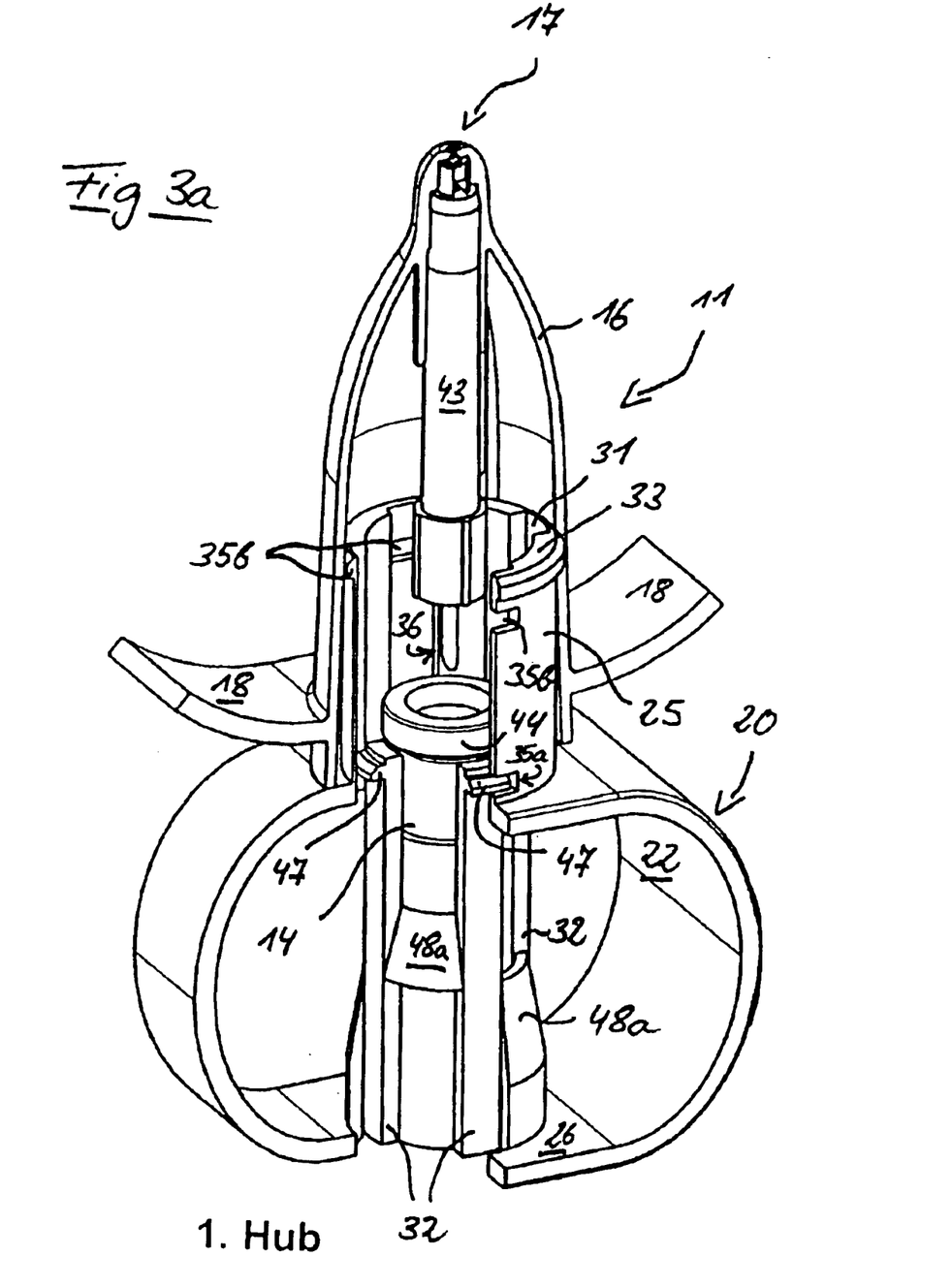
FIG. 3a In different positions and at different operating times, and 3b in each case a part sectional representation of a third embodiment of the invention.
Figure 3B:
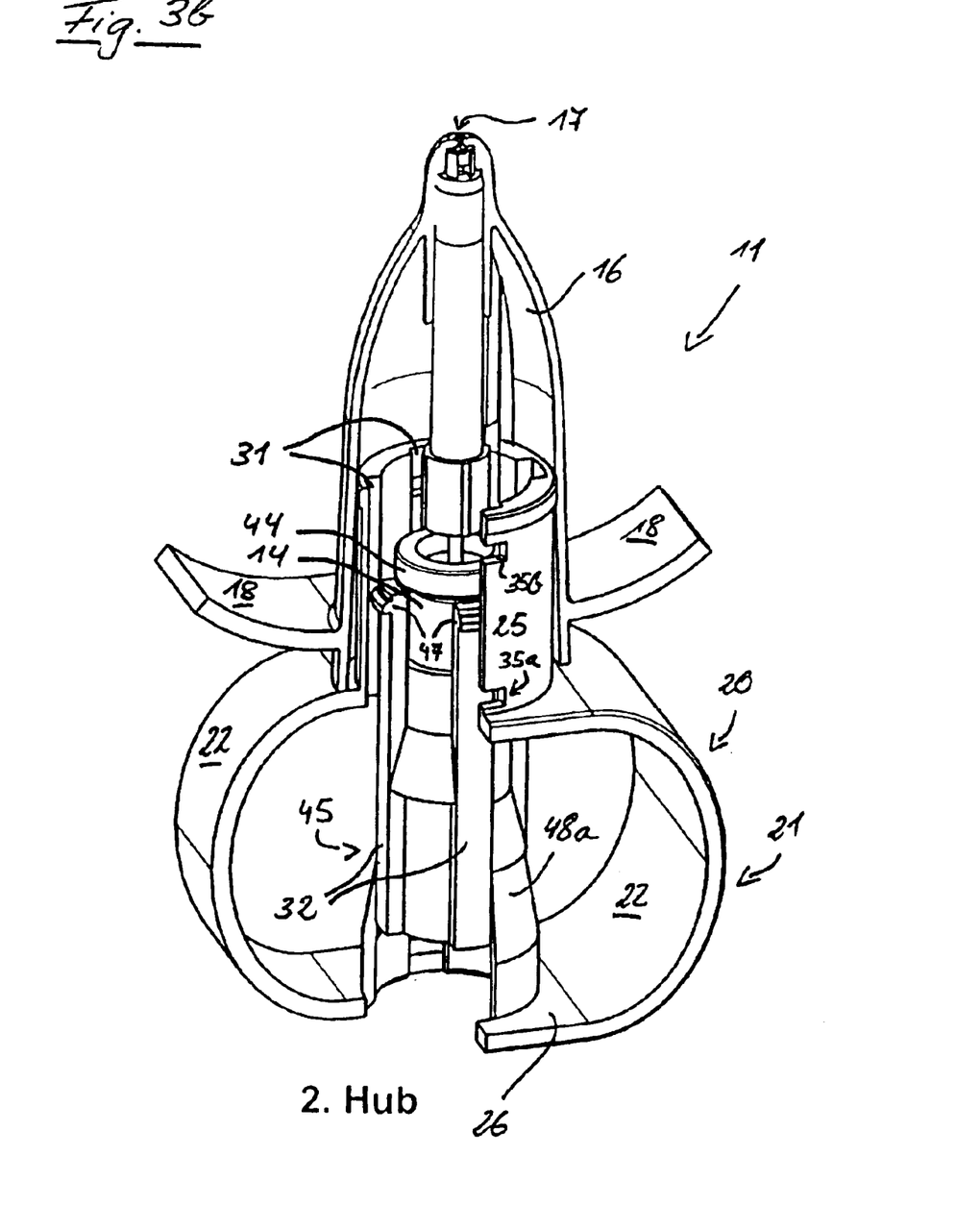

FIGS. 3a and 3b also provide a part sectional view of a third embodiment of the invention, whose essential features once again correspond to the embodiments of FIGS. 1 and 2. Thus, once again reference is made to the description concerning FIG. 1 and hereinafter only the differentiating features are described.

Also in this embodiment the dispenser 11 has a housing, within which there is a piston rod with discharge channel having a discharge opening. The piston rod 43 is once again the piston rod of a thrust piston pump, the discharge channel being constructed on its rear side, remote from the discharge opening 17, as a needle point 36 and consequently can perforate a plug, which is located in the container for sealing the same. On the housing are once again provided laterally projecting back-stops, which through their upwardly curved shape are very suitable for serving as a support for in each case one finger, so that the dispenser can best be held between the index and middle fingers and in this position the actuation of the dispenser by means of the thumb on the base 26 of the actuating means 20 is particularly advantageous.

The actuating means 20 essentially comprise the two webs 22 forming the material bridge 21. At the housing-side end, the two diametrically facing webs 22 are interconnected by means of a ring section 24, whereas at their opposite end remote from the housing side, they issue into an actuating element of the side ring section 46 constructed in the base 26. Coaxially to the central axis of the dispenser, in whose path is also oriented the discharge channel 42, is constructed a guide sleeve 25 projecting from the ring section 24 and used for fixing, particularly the detachable fixing of the ring section 24 to the housing 16. On its front end facing the discharge opening 17, the ring section has a torus 33, which engages in a corresponding groove in the housing 16 and as a result secures the guide sleeve 25. Unlike in the embodiment of FIG. 1 and the embodiment of FIG. 2, the container 14 having the storage chamber 15 storing the medium to be discharged and which simultaneously serves as a pump chamber, is held in a sleeve 45, which projects upwards concentrically to the central axis from the actuating element-side ring section 46. The container edge 44, which can be constructed as a toroidal extension of the external diameter of the container 14, is supported on the sleeve 45. The sleeve 45 is preferably constructed in undetachably connected manner with the actuating means 20 and is preferably shaped onto the latter. The sleeve comprises jacket segments 32 projecting into the guide sleeve 25 and inwardly offset holding webs 48a constructed in areas between the jacket segments 32 and which engage behind the correspondingly constructed scales and backwardly engageable edges 34 on the container outside. In order to obtain a reliable fixing of the container 14 within the dispenser 11 prior to the first actuation, on the outside of the jacket segments 32 are formed detents 47 engaging in locking depressions 35, which are constructed in the guide sleeve 25. In the starting position prior to the first actuation shown in FIG. 3a, the detents 47 engage in the lower locking depressions 35a, whereas after the second actuation they engage in the upper locking depressions 35b, thereby ensuring that after emptying the container is not retracted again through the two proportioned partial strokes. In the intermediate position prior to the second stroke, as shown in FIG. 3b, the detents 47 do not engage behind a locking depression, so that before the second actuation there is no need for pressing over the holding force, as is required for the first actuation, in order to bring about a detachment of the locking action between the detents 47 and the first locking depressions 35a.

During an actuation of the dispenser, an axial guidance of the sleeve 45 is brought about in that the jacket segments 32 are guided in correspondingly constructed guide grooves 31 on the inside in the guide sleeve 26 and as a result an axial twisting of the sleeve 45 relative to the guide sleeve 25 is impossible.

Figure 4:
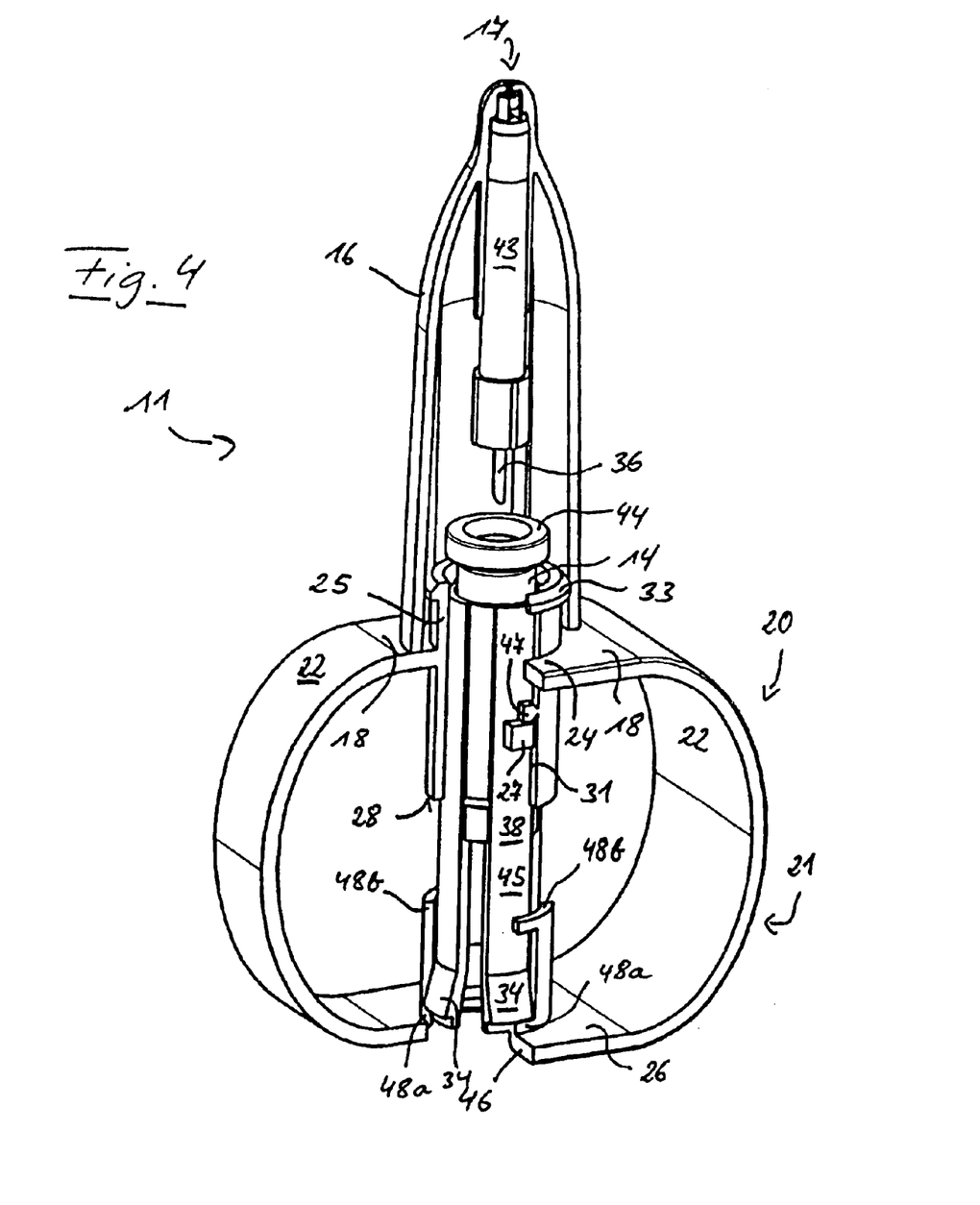
FIG. 4 A fourth embodiment of the invention in a part sectional representation, locking means being provided between the sleeve and housing.

FIG. 4 shows a fourth embodiment of a dispenser according to the invention, which is once again a variant of the embodiments according to FIGS. 1 to 3, to which reference should also be made. FIG. 4 is once again a part sectional representation of the dispenser 11.

Also in the case of this dispenser, the discharge device is constructed as a thrust piston pump, the container serving as the pump chamber. From the discharge opening 17 the piston rod 43 projects inwards into the housing 16 and downwards along the central axis of the dispenser. In the interior of the piston rod 43 is constructed a discharge channel 42, whose lower end, projecting out of the piston rod 43, is constructed as a needle point 36 and is used for perforating a plug 41 arranged in and sealing the interior of the container 14. The plug 41 serves as a piston for the discharge pump and is displaceable by the thrust forces transferred to it by the piston rod 43 in the interior of the container 14 in the sense of reducing the volume of storage chamber 15 of container 14 and as a result brings about a discharge of dischargeable medium. The actuating means 20 is once again essentially formed from two semicircular webs 22, which are constructed as flat bands and which are interconnected at their upper and lower ends in each case by means of a ring section 46, 24. In the vicinity of the housing-side ring section 24 is constructed a guide sleeve 25, which on one side projects above the ring section 24 into the housing 16 and is detachably locked there e.g. by means of a torus 33. However, the locking can also be brought about in that the connection cannot be released again once the locking means has been snapped in. In this case the torus 33 has a corresponding shape, which can engage in a corresponding groove in the vicinity of the housing 16. However, in an area below the ring section 25, the guide sleeve 25 projects downwards towards the lower ring section 46 formed in the base 26. The lower end of the guide sleeve 25 forms the stop edge 28, which limits the travel of an actuating stroke of dispenser 11. On actuating the dispenser, the upper edge of the upper holding webs 48b strike against said stop edge 28. The upper holding webs 48b and the lower holding webs 48a are constructed similar to a double T-beam, said double T-beams being curved corresponding to the configuration of the outer contour of the guide sleeve 25 and the lower T-sections of the double T-beam being shaped or fixed with the lower holding webs 48a on the lower ring section 46 of the actuating element 19, whereas the upper T-sections forming the upper holding webs 48b project upwards to the stop edge 28 of the guide sleeve 25. The container 14 storing the medium in its storage chamber 15 is placed in a ring body 38, which has a sleeve-like construction and which is provided at its lower end with outwardly projecting scales 34 behind which can engage the holding webs 48a, 48b. Prior to the first actuation of the dispenser 11, the first holding webs 48a engage behind the scale 34 on the lower edge of the ring body 38, whilst prior to the second actuation the holding webs 48 engage behind said scales 34 and during the return stroke it is ensured that the ring body 38 cannot move back. As a result of the pretension of the webs 22 the base 26 from which the holding webs 48 project is moved back and consequently during the return stroke the front holding webs 48*b* are initially guided behind the scales 34 and engage behind the same during a second actuating stroke.

From the ring body 38 project outwards sliding pieces 27, which are guided in correspondingly constructed guide grooves 31 of the guide sleeve 25. Into the movement path of the sliding pieces 27 project detents 47, which are connected by nominal breaking points to the guide sleeve 25. An actuation of the dispenser is only possible if a minimum actuating force is applied and as a result the detents 47 are sheared at the breaking points and the sliding piece can be moved on further in the guide groove 31. This ensures that application takes place of a minimum actuating force, which is sufficient to perform in a complete and uninterrupted manner a discharge stroke, so that there is no performance of partial discharges in that during an actuation of the actuating means 20 only part of the possible actuating path is covered. Once again the container 14 is held by means of a torus 44 in the ring body 38.

This dispenser can be manufactured and completed in simple manner in that initially the container 14 is inserted in the ring body 38 and the latter is then introduced by the lower ring section 46 into the dispenser to such an extent that the lower, first holding webs 48*a* engage behind the scale 34 at the rear end of the ring body 38. It must be ensured that the sliding pieces 27 are cleanly inserted into the guide grooves 31 of the guide sleeve 25. Then the housing 16 can now be mounted on the actuating means 20 now provided with the container 14. The torus 33 of the guide sleeve 25 engages behind a groove constructed in the interior of the housing 16. For actuating the dispenser, planar surfaces of the webs 22 formed in the area of the ring section 24 serve as back-stops 18 and on them can be placed the fingers of the user. These are preferably constituted by the index and middle fingers, which engage on either side of the housing 16. The initiation of the actuating force takes place by introducing a force on the base 26 at the other end of the two webs 22. The two webs 22 form a material bridge 21 between the base of the actuating element and the housing 16.

Figure 5:
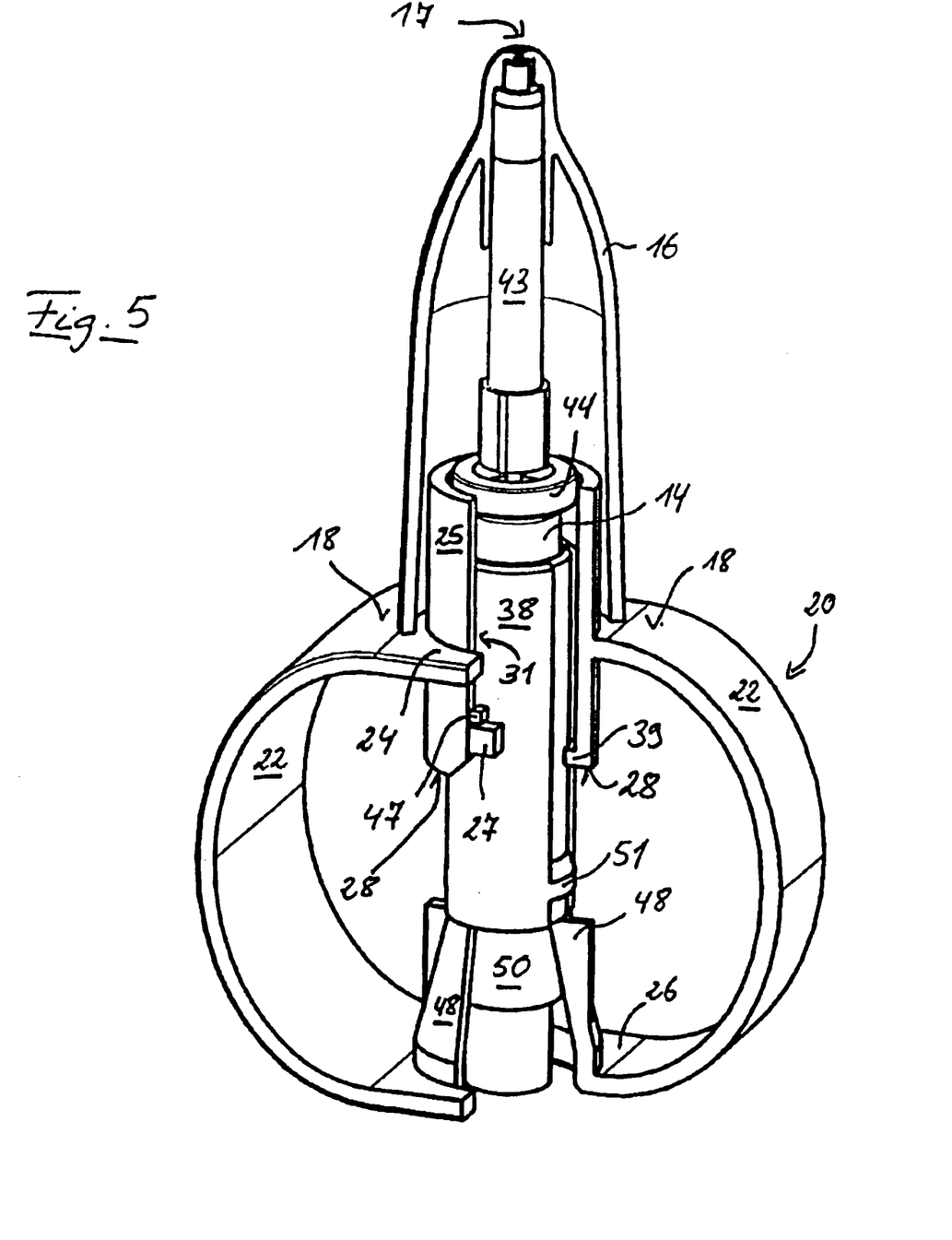
FIG. 5 A fifth embodiment of the invention, which is a variant of that of FIG. 4.

FIG. 5 shows in part sectional form a fifth embodiment of a dispenser according to the invention. The embodiment of FIG. 5 is a variant of that according to FIG. 4 and which essentially only differs from the latter in the way in which the force is transferred from the actuating means 20 to the ring body 38. Here the ring body 38 has at its rear end an at least once and preferably multiple conical area, the conical portions being arranged in frustum-shaped, coaxially succeeding manner and each of the truncated cones 58 is engaged behind by the holding web 48 during an actuation of the dispenser 11. During the return stroke the holding web 48, which can in particular be constructed as a tapering, frustum-shaped, but elastically outwardly yielding portion, along the outer contour of the following truncated cone 50 and engages behind its lower, further rearwardly located base surface at the end of the return stroke and can consequently initiate on the following frustum portion 50 the actuating force for the following actuating stroke on the ring body 38. Thus and not only as shown in FIG. 5, there can not only be two proportioned partial actuations of the dispenser, but also numerous further actuations. The limitation of the actuation path once again takes place through the spacing from the upper edge of the holding web 38 to the stop edge 28 on the rear, lower end of the guide sleeve 25. In the guide sleeve 25 are once again formed guide grooves 31 in which can travel the sliding pieces 27 formed externally on the ring body 38 and it is once again possible for detents 47 shearable at nominal breaking points to project into said guide grooves 31 and consequently initially the shearing forces for shearing the detents 47 must be applied, which ensures that a continuous actuating stroke is performed, during which the necessary deforming forces are applied, so that the webs are more strongly curved enabling the upper edge of the holding webs 48 to engage on the stop edge 28 and reliably ensure an automatic return stroke.

In the embodiment shown in FIG. 5 the actuating means 20 is not only connected by means of the guide sleeve 25 to the housing 16, but instead the latter is continuously constructed with the actuating means 20 in the vicinity of the lower end of the housing 16 alongside the ring section 24 interconnecting the webs. This can be both an undetachable interconnection of the two parts, e.g. by welding or bonding, or a one-piece connection of the two areas.

To ensure a termination of an undesired moving back of the ring body 38 following the last actuation of the dispenser 11, which can lead to a discharge, on its rear section the ring body 38 has a securing web 51 upstream of the frustum sections 50 and which after the final actuation can be engaged behind by the gripping elements 39, which project inwards from the guide sleeve 25 and which can be constructed on the rear end thereof and consequently a return movement of the ring body 38 is prevented.

FIG. 6 once again shows in part sectional form another embodiment of the invention, which differs from the embodiments according to FIGS. 1 to 5 and 7 and 8 in that the material bridge 21 is constructed in the form of a bellows 29 and not material webs 22.

In accordance with the embodiments according to FIGS. 1 to 5, the dispenser 11 once again has a housing 16 provided with a discharge opening 17. To the latter leads a discharge channel, which can be connected to the storage chamber 15 of a container 14. The storage chamber 15 e.g. stores a liquid 12, which can be discharged by the dispenser through the discharge opening 17. The container is sealed by a plug 41, which seals the storage chamber 15 of the container and which can be perforated by a needle point 16 constructed on the discharge channel side. Through this perforation of the plug 22, it is possible to produce a fluidic connection for the medium to be discharged between the storage chamber 15 and the discharge opening 17. The housing 16 projects downwards, so that also over and beyond the length of the container 14, the housing radially encloses the same. In this area of the housing are formed guide grooves 31, in which are formed detents 47 which can be overtravelled or torn off at nominal breaking points. In the interior of the housing the container 14 is held in a ring body 38, which is axially displaceable with respect to the housing in the direction of the discharge opening 17. The guide grooves 31 are traversed by holding webs 52, which project laterally from the lower end of the ring body 38. At the outer end of the holding webs 52 are formed dogs 53, behind which can engage the holding webs 48. The holding webs 48 project upwards from the base surface 26 in the vicinity of a ring section 46. For actuating the dispenser and producing a discharge stroke, the forces introduced on the base 26 by the user must be sufficient for the holding webs 42 in the area in which they traverse the guide groove 31 to overtravel or shear the detents 47. Further detents 47 located in the further path of the guide groove 31 ensure a stoppage of the stroke movement and the actuating force then introduced, reduced by the already produced pretension of the bellows 29 is no longer sufficient to press over this stop catch. Thus, as from the first discharge a return stroke occurs, in which initially the front, second holding web 48b is moved back behind the dog 53 and engages behind the same and consequently during the next actuation transfers the actuating force thereto and consequently passes it on to the ring body 38.

Figure 6:
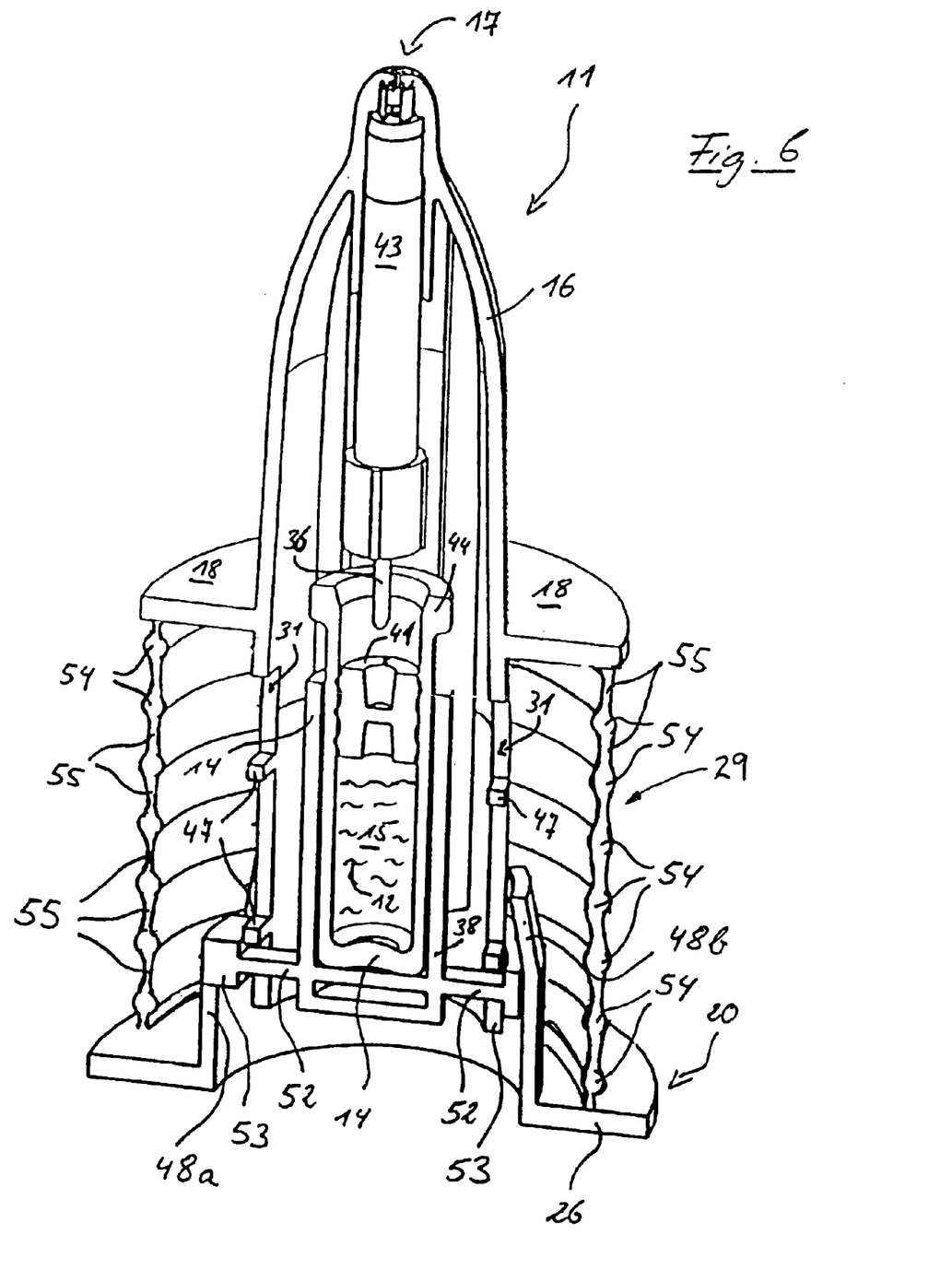
FIG. 6 A sixth embodiment of the invention with a bellows as the spring element.

Between the lower edge of the annular back-stop 18 projecting radially outwards from the housing 16, extends downwards to the base 26, which is also constructed as an annular disk, the bellows 29. The bellows 29 has a coiled fold configuration, the coiling in particular existing of a material thickening 54 and between two material thickenings 54 there is always a thinner material area 55 and in this way a closed bellows is formed, which can reduce its length by an inward kinking towards the container 14 and deformation of the thinner areas 55, so that a pretension occurs, which ensures an automatic return stroke at the end of an actuating stroke. The material from which the bellows is made and which can in particular be a plastic, must have an adequate elasticity and at the same time an adequate stiffness. In order to reinforce the effect of the elasticity and stiffness, in the interior of the bellows 29 and in particular in the interior of the thickenings 54 can be provided a metal spiral spring, e.g. of spring steel, the thickenings 54 being themselves constructed in the manner of a spiral spring and can be made from a different plastics material to the thinner wall sections 55 and can ensure the necessary spring effect. A construction of such a dispenser is also conceivable, where the bellows 29 is replaced by a spiral spring element, which can be in the form of either a plastic spiral spring or a spring steel spiral spring. However, it is important that the spiral spring is suitable for maintaining in fixed form the actuating means 20, which is essentially formed by the base 26, on the housing 19, particularly on the lower edge of the back-stop 18. This retention effect can e.g. be obtained by bonding or welding. For this purpose the bellows is initially welded to the lower edge of the back-stop 18 and then following the introduction of the container 14 into the ring body 38 and the insertion of the latter into the guide grooves and consequently into the housing 16, the base 26 is mounted and then the still free side of the bellows 29 is welded to the base 26 of the actuating means 20.

FIGS. 7 and 8 once again show embodiments of a dispenser according to the invention and are essentially modifications of the embodiments of FIGS. 1 to 4 and reference is additionally made to the description concerning the latter.

Figure 7:
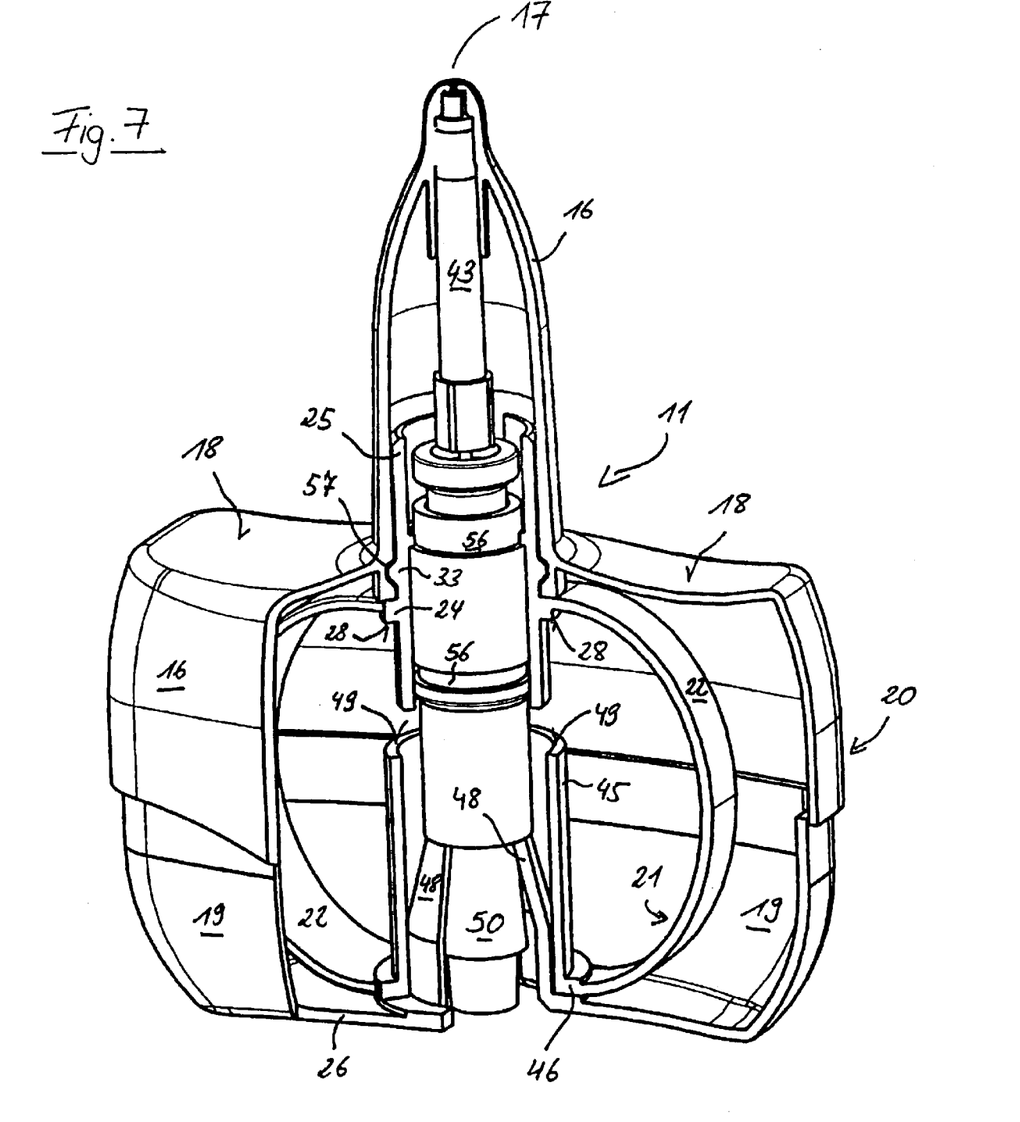
FIG. 7 A seventh embodiment of the invention, the material webs being covered by an actuating element.
Figure 8:
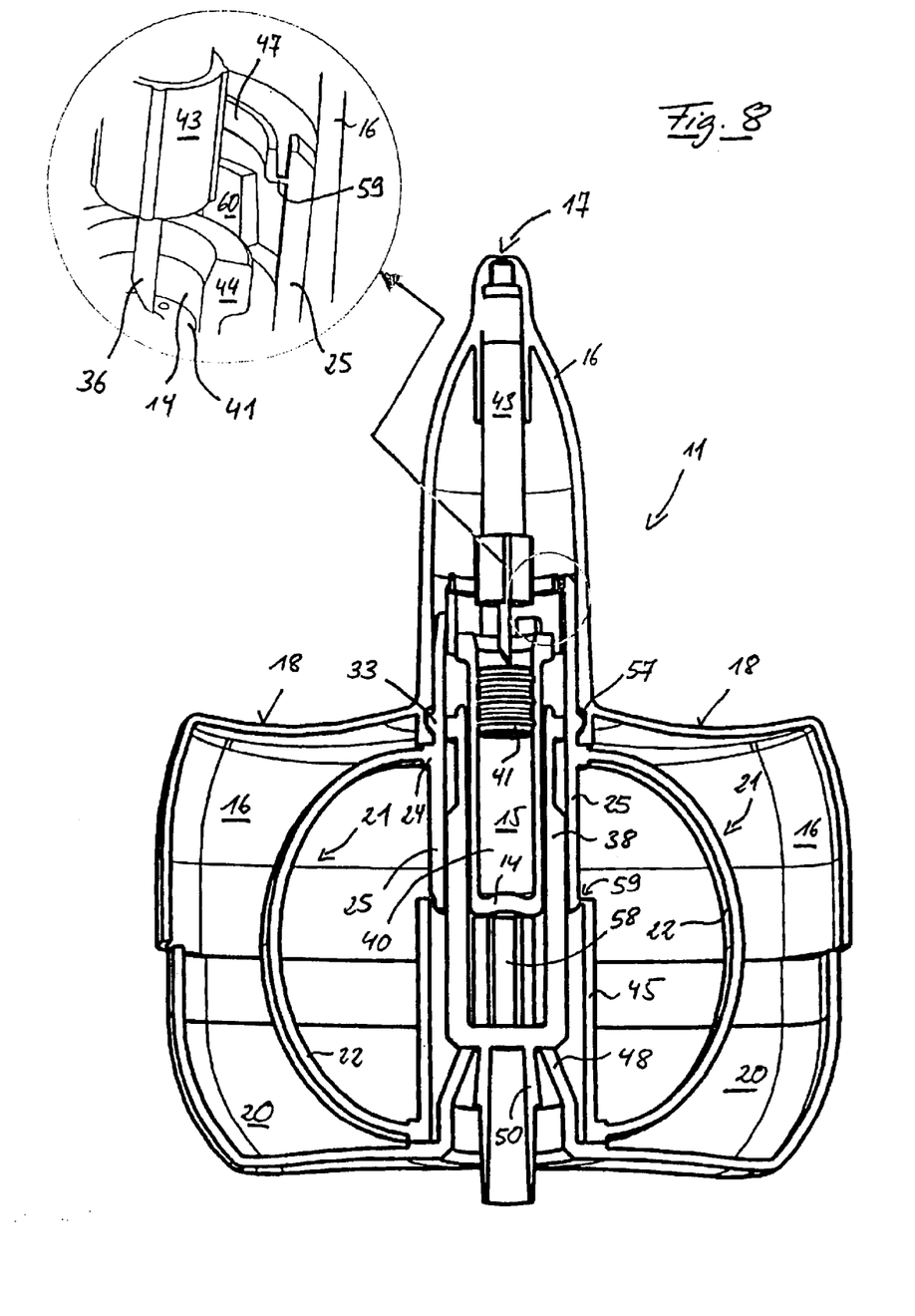
FIG. 8 A modification of the embodiment according to FIG. 7 with a different mounting support and guide for the container in the dispenser.

Unlike in the case of the embodiments according to FIGS. 1 to 4, the dispensers 11 according to FIGS. 7 and 8 are provided on the actuating means 20 with an actuating element 19, which covers the material bridge 21, formed from webs 22 and which link the housing 19 to the actuating means 20, in the areas where the housing 16 does not cover the same, so that an outwardly closed body only having flat elements is formed for the dispenser 11.

The actuating means 20 together with its actuating element 19 is fixed by means of the guide sleeve 25 in the housing 16. For this purpose on the outside of the guide sleeve 25 is provided a torus 33, which can engage with a corresponding holding groove 57 in the housing. As a function of the design of the torus 33 and holding groove 37 said connection can be both detachable and undetachable. Additionally or alternatively the torus 33 and holding groove 57 can be replaced by a bonding or welding together of the two parts. In engagement with the lower end of the housing 16 is provided the housing-side ring section 24 from which project the two band-shaped webs 22, which are curved in an approximately semicircular manner and through the deformation of the webs, namely by increasing the radius of curvature, a pretension is produced during the actuation of the dispenser 11. At the end of the webs 22 remote from the housing they are interconnected by means of the actuating means-side ring section 46. The actuating element 19 is fixed from the actuating means-side torus 46. The fixing is in particular undetachable, e.g. by welding or bonding. In the interior of the webs 22, the sleeve 45 projects upwards in the direction of the housing-side ring section 24 from the lower, actuating element-side ring section 46. The housing-side ring section 24 is constructed on its underside as a stop edge 28 and as a result of the spacing between the latter and the upper edge of the sleeve 45, which forms the counterstop, the actuating stroke path is limited.

In the interior of the guide sleeve 25 is provided a ring body 38, in which is held the container 14. Onto the lower edge of the ring section 38 are shaped truncated cones 50, which can be engaged behind by holding webs 48, which are constructed so as to project inwards and concentrically surround the truncated cones. Initially the sleeve 38 is moved into the dispenser to such an extent that the holding webs 48 engage behind the underside of the ring body 38. During the actuation of the dispenser at the actuating element 19, the latter is moved towards the discharge opening 17. The holding webs 48 engage behind the ring body 38 and move it upwards towards the discharge opening. During this movement the sleeve 14 is carried along, so that initially the needle point 36 perforates the plug 41 sealing the container 14 and consequently produces the fluidic connection between the discharge channel 42 and the storage chamber 15 of container 14. During the subsequent displacement of the plug 41 in the container 14, the volume of the storage chamber 15 is reduced and there is a discharge of medium through the discharge channel 42 to the discharge opening 17, where there is in particular an atomized discharge of the medium. At the end of the actuating stroke the upper edge 49 of sleeve 45 reaches the stop 28. A further actuation is not possible and by means of this free path the volume of a discharge stroke and consequently the medium portion to be discharged is determined. The webs 22 are deformed during this actuation. As a result of the elastic deformation of the webs 22, which consequently represent a force reservoir, energy is absorbed and is used to bring about an automatic return of the actuating element 19 to its starting position. The holding webs 48 slide rearwards over the outer surface of the truncated cones to such an extent that the holding webs 48 engage behind the underside of the following truncated cone. The length of a truncated cone 50 must be matched to an actuating stroke path. During this return stroke the position of the ring body 38 relative to the discharge opening 17 is not changed, so that during a following actuation there is once again a reduction of the volume of the storage chamber 15 corresponding to the stroke of the dispenser. This ensures that during each dispenser actuation there is a discharge of an equal volume, i.e. an equal medium portion.

In the construction according to FIG. 7 for the purpose of fixing the ring body 38 in the interior of the guide sleeve 25, on the latter is provided a detent 47 constructed as an inwardly projecting ring and which engages in the ring grooves 56, which are in each case spaced from one another by an actuating stroke path. Through the engagement of the detents 47 in the ring groove 56 it is ensured that the ring body 38 can no longer be jointly moved back during the return stroke and consequently there is no change to the relative position between the container 14 and the discharge opening 17 in housing 16. In conjunction with the ring grooves 56, the detents 47 also ensure that for overtravelling the ring grooves 56 an actuating force exceeding a minimum amount must be applied to the ring body 38. This actuating force is chosen in such a way that during such an actuation there is always a complete discharge stroke, which is limited by the stroke path and there are no partial actuations, where the complete stroke of the dispenser is not utilized and consequently there is not a complete portioned discharge.

The embodiment of FIG. 8 is only slightly modified compared with that of FIG. 7. The part sectional representation uses a different intersection line. It is also apparent in FIG. 8 how the plug 41 seals the storage chamber 15 of the container 14 and how the container 14 is also suitable for simultaneously forming the pump chamber 40 of the discharge device. FIG. 8 also makes it clear how the container 14 is held in the ring body 38, which here has a saucer-shaped construction and is provided with a terminating base. From said base can project upwards shortening pieces 58 on which stand the container 14, so that with a minimum of constructional changes different volumes of the container 14 can be used and in this case it is necessary to adapt the spacing between the upper edge 49 and the stop edge 28 of the sleeve 45, which serves as a stop member.

FIG. 8 also shows how the holding webs 48 engaging behind the ring body 38 for an initial actuation, during a further actuation can then initially engage behind the first and optionally further truncated cones 50. Although FIG. 8 only shows a single truncated cone which can be engaged behind, so that it is only possible to perform two discharge strokes with equal, proportioned medium discharges, through an increase in the number of truncated cones it is also possible to permit the discharge of a larger number of proportioned discharge strokes, the length of a truncated cone being reduced in accordance with the adaptation of the length of the corresponding actuating stroke to the number of partial discharges. The quantity discharged during a partial actuation, as a result of predetermined details concerning the actuating stroke path, can be varied on the basis of design standpoints in that the internal diameter of the container 14 is increased and therefore the storage chamber 15 of said container 14 has a larger volume for the same actuating stroke path.

Unlike in the construction according to FIG. 8, prior to performing a first actuating stroke, the sleeve 45 is connected by means of a nominal breaking point 59 with the guide sleeve 25. If an adequate actuating force is applied to the actuating element 19, said breaking point indicates the application of a gripping shell.

FIG. 8 shows how, by means of the detent 47 constructed as an annular body and which is also connected by a nominal breaking point 59 to the housing 16, it is possible to produce a threshold force for the second actuation of the dispenser. The second dispenser discharge stroke can only take place if perforation is brought about by the ram 60 indirectly connected to the container 14. For this purpose it is necessary to apply an adequately high actuating force to the actuating element 19. The nominal breaking point 59 then tears and the annular detent 47 can be moved upwards in housing 16 towards the discharge opening.

In the larger-scale, partial representation it is also possible to see the plug 41 held in the container 14 and on whose upper end is formed a container edge 44. The plug is perforated by the discharge channel constructed in this area as a needle point 36 as soon as the first dispenser actuation takes place.

An advantage of the embodiment according to FIGS. 7 and 8 is that the webs 22 forming the material bridge are housed in a closed space, which is sealed from the outside either by the housing 16 or by the actuating element 19. Thus, the user has no access possibility to the webs 22 and can consequently cause no damage or blockage to these important functional elements. It is not relevant for the construction of this feature whether the material bridge 21 is constructed in the form of band-shaped webs 22 or whether it is e.g. in the form of a bellows, such as is e.g. shown in FIG. 6. The advantages of a closed construction also apply in the latter case.

FIGS. 1 to 8 show different embodiments of the same operating principle and in each case there are only modifications concerning the movement sequence and in the design of movement sequence-influencing elements in the form of link guides, stop edges, holding elements, rear engagements and different possibilities for introducing forces. Obviously further developments are conceivable which form the basis for the invention and make use of the claimed operating principle.

I claim:

1. Dispenser for media, comprising a housing (16) and actuating means (20) having an actuating pusher for manually actuating a pump including a pump chamber (40) and a pump piston (41), the pump cylinder containing at least two partial charges of the medium to be dispensed, the charges being dispensed in subsequent actuations of the pump by causing at least two subsequent partial strokes of relative movement of predetermined length between piston (41) and pump chamber to advance the piston in the chamber (40) from a rest position to an advanced position without a return stroke of the piston, the actuating means including an actuating means return stroke mechanism having advancing means for advancing the piston and including idling means for returning the actuation means into the rest position without returning the piston from its advanced position, the actuating means return stroke mechanism including an elastically deformable curved material bridge (21) acting between the actuation pusher and the housing (16) as a return spring for returning the actuation means.

2. Dispenser according to claim 1, wherein the material bridge (21) is formed from at least one web (22).

3. Dispenser according to claim 2, wherein on a ring section (24) is provided a guide sleeve (25), which is constructed coaxially to the central axis and projects into the interior of the housing (16).

4. Dispenser according to claim 1, wherein at least two webs (22) are provided, said a least two webs (22) being uniformly distributed in rotationally symmetrical manner about a central axis.

5. Dispenser according to claim 1, wherein, in the relaxed state, said at least one web (22) is approximately arcuate.

6. Dispenser according to claim 1, wherein ends of the said at least one web (22) facing the housing (16) meets in a ring section (24).

7. Dispenser according to claim 6, wherein the ring section (24) facing the housing (16) is supported on the housing.

8. Dispenser according to claim 6, wherein the ring section (24) facing the housing (16) is integral with the housing (16).

9. Dispenser according to claim 6, wherein the ring section (24) facing the housing (16) is detachably fixed to the housing (16).

10. Dispenser according to claim 1, wherein the material bridge (21) is made from a breaking-resistant plastic.

11. Dispenser according to claim 1 further comprising a plug (41) being the pump piston sealingly closing the pump chamber (40), a discharge channel (42) in the housing (16) leading to the discharge opening (17) being provided in a piston rod (43) perforating during a first actuation the plug (41) and producing the connection between the pump chamber (40) and the discharge opening (17) and subsequently during actuation acting on the piston in such a way that the piston is moved into the pump chamber (40) to reduce the volume of the pump chamber (40).

12. Dispenser according to claim 1, wherein the pump chamber (40) is held in a sleeve (45), which is displaceably guided with respect to the housing (16).

13. Dispenser according to claim 1, wherein the pump chamber (40) can be introduced into the dispenser (11) through an opening, particularly through an actuating element-side ring section (46).

14. Dispenser according to claim 1, wherein at least one of locking and stop means (49), which at least serve to limit an actuating stroke, act at least indirectly between the actuating means (19) and the housing (16).

15. Dispenser according to claim 1, wherein at least one of locking and stop means, which act against a return stroke of the container (14) during the return stroke of the actuating element (19), act at least indirectly between the actuating means (20) and the housing (16).

16. Dispenser according to claim 1, wherein locking means (37), which must be pressed over for producing an actuating stroke of the actuating means (19), act at least indirectly between the actuating means (20) and the housing (16).

17. Dispenser according to claim 1, wherein the material bridge (21) serves as the actuating means.

18. Dispenser according to claim 1, wherein the area of the material bridge (21) engaging on the housing (16) is constructed as a back-stop (18).

19. Dispenser according to claim 1, wherein in the area not covered by the housing (16), the material bridge (21) is surrounded by an actuating element (19).

20. Dispenser according to claim 1, wherein a back-stop (18) is formed on the housing (16).

* * * * *